(12) United States Patent
Osada et al.

(10) Patent No.: US 6,670,187 B2
(45) Date of Patent: Dec. 30, 2003

(54) MUTANT PLK PROTEIN AND GENE ENCODING THE SAME

(75) Inventors: Hiroyuki Osada, Niiza (JP); Siro Simizu, Tokorozawa (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/866,590

(22) Filed: May 30, 2001

(65) Prior Publication Data

US 2002/0076713 A1 Jun. 20, 2002

(30) Foreign Application Priority Data

May 31, 2000 (JP) .................................. 2000-163122

(51) Int. Cl.[7] .................. C12N 15/87; C12N 9/12; C12N 15/12; C12N 15/54; C07K 14/435
(52) U.S. Cl. .................. 435/455; 435/194; 536/23.5; 536/23.2; 530/350
(58) Field of Search ................. 530/350; 435/194, 435/69.1, 183, 455; 536/23.2, 23.5

(56) References Cited

U.S. PATENT DOCUMENTS 6,180,380 B1    1/2001   Strebhardt et al.

FOREIGN PATENT DOCUMENTS

WO          95/06734       3/1995

OTHER PUBLICATIONS

Knecht et al., Cancer Research 59 (12):p2794–2797 Jun. 15, 1999.*
Wolf et al., Oncogene, 1997, V14, N5 (FEB 6), P543–549.*
Yuan et al., American Journal of Pathology 150 (4):p1165–1172 1997.*
Strebhardt et al., Journal of Cellular Biochemistry Supplement 0 (18D):p103 1994Conference/Meeting: Keystone Symposium on Molecular Basis of Cancer Therapy Tamarron, Colorado, USA Mar. 4–10, 1994.*
Teillac et al., Annales d'urologie (France) 1990, 24 (1) Abstract only.*
Golsteyn et al., *Journal of Cell Science*, 107, pp. 1509–1517 (1994).
Hamanaka et al., *The Cell Growth & Differentiation*, vol. 5, pp. 249–257 (1994).
Lane et al., *Journal of Cell Biology*, vol. 135, No. 6, Part 2, pp. 1701–1713 (1996).

(List continued on next page.)

*Primary Examiner*—Mary E. Mosher
*Assistant Examiner*—Misook Yu
(74) *Attorney, Agent, or Firm*—Greenblum & Bernstein, P.L.C.

(57) ABSTRACT

A mutant Plk protein having a mutation in C-terminal domain thereof specified by amino acid residues of from 439 to 603 of amino acid sequence of wild-type Plk protein wherein said mutation decreases affinity with Hsp90 protein, and a gene encoding said mutant Plk protein are provided. A method for detecting an abnormal cell which comprises the step of detecting the mutant Plk protein or the gene encoding the protein is also provided.

7 Claims, 4 Drawing Sheets

OTHER PUBLICATIONS

Lee et al., *Proc. Natl. Acad. Sci. USA*, vol. 96, No. 25, pp. 14360–14365 (1999).

Ferris et al., *Biochemical and Biophysical Research Communications*, vol. 252, pp. 340–344 (1998).

Feng et al., *Biochem. J.*, 339, pp 435–442 (1999).

Buchner, *Tibs*, 24, pp. 136–141 (1999).

Kimura et al. *Protein, Nucleic Acid, Enzyme*, 41, pp. 883–887 (1996).

Suggs et al., *Proc. Natl. Acad. Sci. USA*, vol. 78, No. 11, pp. 6613–6617 (1981).

Young et al., *Science*, vol. 222, pp. 778–782 (1983).

Horii, *Experimental Medicine*, vol. 12, No. 6, pp. 35–38 (1994).

Frohman et al., *Proc. Natl. Acad. Sci. USA*, vol. 85, pp. 8998–9002 (1988).

Sanger et al., *Proc. Natl. Acad. Sci. USA*, vol. 74, No. 12, pp. 5463–5467 (1977).

Maxam et al., *Methods in Enzymology*, vol. 65, pp. 499–560 (1980).

Wang et al., *Science*, vol. 224, pp. 1431–1433 (1984).

Kato et al., *Biochemical and Biophysical Research Communications*, vol. 130, No. 2, pp. 692–699 (1985).

Robb et al., *Proc. Natl. Acad. Sci. USA*, vol. 80, pp. 5990–5994 (1983).

Gluzman, *Cell*, vol. 23, pp. 175–182 (1981).

Urlaub et al., *Proc. Natl. Acad. Sci. USA*, vol. 77, pp. 4216–4220 (1980).

Kinoshita et al., *Clin. Chim. Acta*, vol. 228, pp. 83–90 (1994).

Orita et al., *Genomics*, vol. 5, pp. 874–879 (1989).

Schulte et al., *The Journal of Biological Chemistry*, vol. 270, No. 41, pp. 24855–24588 (1995).

Hutchison et al., *The Journal of Biological Chemistry*, vol. 267, No. 20, pp. 13952–13957 (1992).

Caplan, *Trends in Cell Biology*, vol. 9, pp. 262–268 (1999).

Whitesell et al., *Proc. Natl. Acad. Sci. USA*, vol. 91, pp. 8324–8328 (1994).

Schulte et al., *Molecular and Cellular Biology*, vol. 16, No. 10, pp. 5839–5845 (1996).

Dai et al., *The Journal of Biological Chemistry*, vol. 271, No. 36, pp. 22030–22034 (1996).

Sharma et al., *Oncogene*, vol. 16, pp. 2639–2645 (1998).

Schulte et al., *Biochemical and Biophysical Research Communications*, vol. 239, pp. 655–659 (1997).

Golsteyn et al., *The Journal of Cell Biology*, vol. 129, No. 6, pp. 1617–1628 (1995).

K.E. Mundt et al., "On the Regulation and Function of Human Polo–Like Kinase 1 (PLK1): Effects of Overexpression on Cell Cycle Progression", *Biochemical and Biophysical Research Communications*, vol. 239, No. 2, pp. 377–385 (1997).

Kyung S. Lee et al., "Plk Is A Functional Homolog of Saccharomyces cerevisiae Cdc5, and Elevated Plk Activity Induces Multiple Septation Structures", *Molecular and Cellular Biology*, vol. 17, No. 6, pp. 3408–3417 (1997).

Siro Simizu et al., "Mutations in the Plk Gene Lead to Instability of Plk Protein in Human Tumour Cell Lines", *Nature Cell Biology*, vol. 2, No. 11, pp. 852–854 (2000).

Roy M. Golsteyn et al., "Cell Cycle Analysis and Chromosomal Localization of Human Plk1, A Putative Homologue of the Mitotic Kinases Drosophila Polo and Saccharomyces", *Journal of Cell Science*, vol. 107, No. 6, pp. 1509–1517 (1994).

Johannes Buchner, "Hsp90 & Co.—A Holding for Folding", *TIBS: Trends in Biochemical Sciences, Elsevier Publication, Cambridge, En.*, vol. 24, No. 4, pp. 136–141 (1999).

Saiki et al., *Science*, vol. 230, pp. 1350–1354(1985).

Togashi et al., *Oncology Research*, vol. 10, pp. 449–453(1998).

\* cited by examiner

Fig. 4
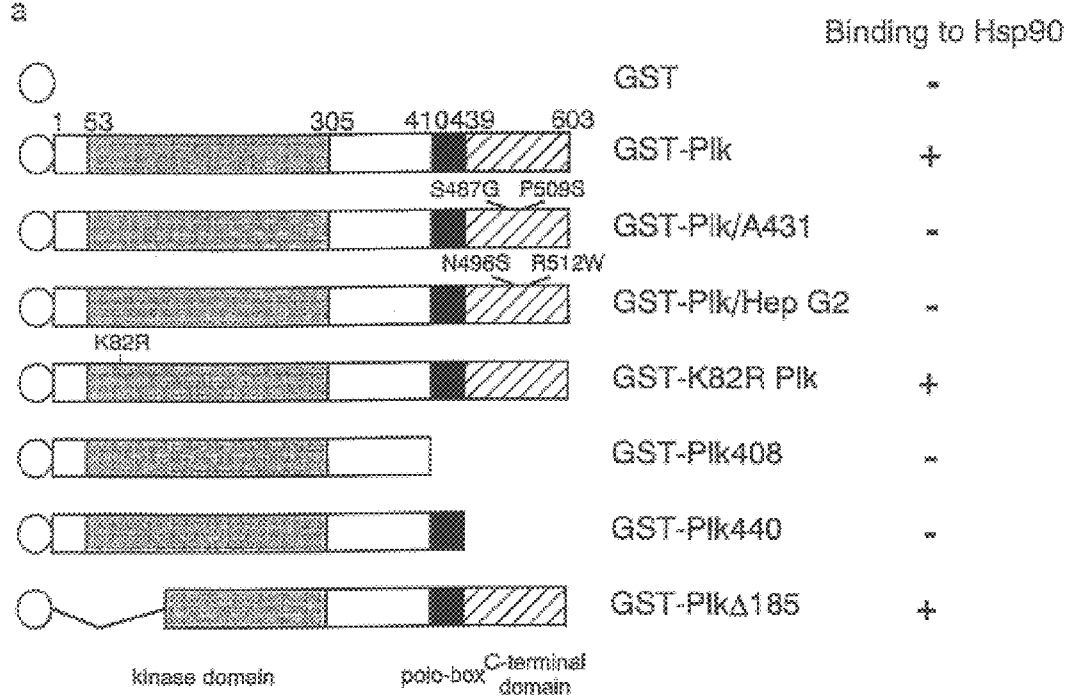
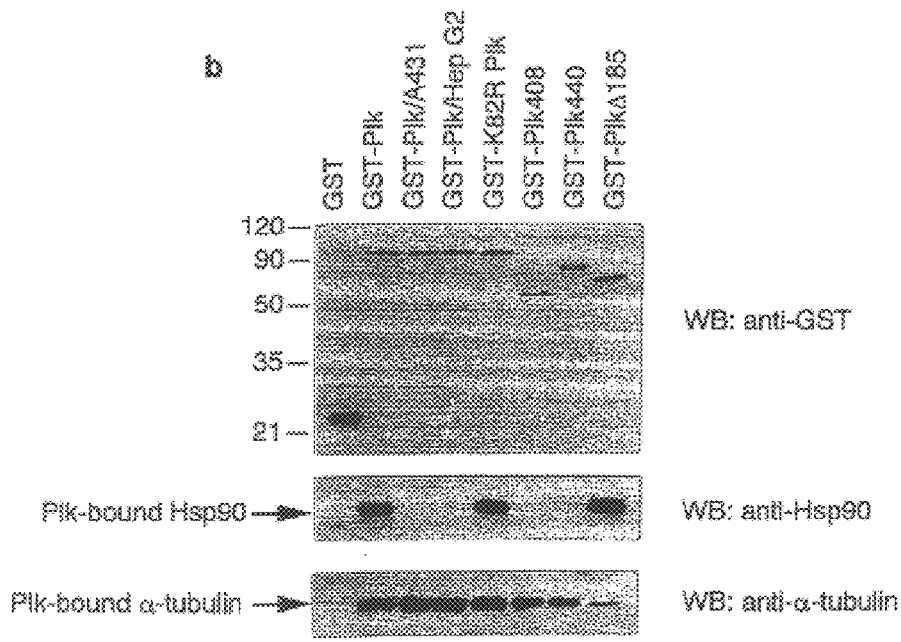

```
                        SEQUENCE LISTING

<160> NUMBER OF SEQ ID NOS: 2

<210> SEQ ID NO 1
<211> LENGTH: 23
<212> TYPE: DNA
<213> ORGANISM: Human

<400> SEQUENCE: 1
catgagtgct gcagtgactg cag                                            23

<210> SEQ ID NO 2
<211> LENGTH: 22
<212> TYPE: DNA
<213> ORGANISM: Human

<400> SEQUENCE: 2
gacaaggctg tagaacccac ac                                             22
```

MUTANT PLK PROTEIN AND GENE ENCODING THE SAME

FIELD OF THE INVENTION

The present invention relates to the Plk protein having mutation(s) and the gene encoding said protein.

BACKGROUND ART

Polo gene which acts during mitosis in a Drosophila cell has been reported. As a human gene similar to the Polo gene, Plk gene is known which comprises 2137 nucleotides (whole cDNA sequence) including a coding region consisting of 1809 nucleotides and encodes a protein of 603 amino acids (Golsteyn, R. M., et al., J. Cell Sci., 107, 1509–1517, 1994; Hamanaka, R., et al., Cell Growth Differ., 5, 249–257, 1994). When the function of protein is inhibited by antibody, abnormal cell division is observed (Lane, H. A. and Nigg, E. A., J.Cell Biol., 135, 1701–1713, 1996).

The Plk gene is a phosphorylation enzyme having a kinase domain at its N-terminus. The gene also has a domain called polo-box in its middle, which has been revealed to participate in localization of the protein (Lee, K. S., et al., Proc. Natl. Acad. Sci. USA, 96, 14360–14365, 1999). Furthermore, it has been shown that a proteasome is involved in degradation of the Plk protein (Ferris., D. K., et al., Biochem. Biophys. Res. Commun., 252, 340–344, 1998); and that the Plk protein is associated with tubulin which is a cytoskeleton (Feng, Y., et al., Biochem. J., 339, 435–442, 1999). Thus, Plk is considered to be subjected to various regulation and to control the progress of cell cycles. However, physiological roles, functions and the like of the Plk gene remain unknown at present, and elucidation of these features has been desired in the fields of basic scientific researches, biology, pharmaceuticals and the like.

DISCLOSURE OF THE INVENTION

The inventors of the present invention have conducted various studies on physiological functions of the Plk protein, and found that Hsp90 protein, a molecular chaperone which interacts with various protein molecules, was involved in stabilization of Plk protein; and that Hsp90 protein binds to the C-terminal domain of the Plk protein so as to stabilize the protein. The inventors conducted further studies and found that the Plk protein having mutation(s) at the C-terminal domain was present in malignant tumor cells. They also found that affinity of the mutant protein with Hsp90 decreases, which resulted in lack of stabilization of the Plk protein. The present invention was achieved on the basis of these findings.

The present invention thus provides the mutant Plk protein having mutation(s) in the C-terminal domain specified by amino acid residues of from 439 to 603 of the amino acid sequence of the Plk protein, wherein the mutation(s) decreases affinity with Hsp90; and the gene encoding said mutant Plk protein. The aforementioned mutant Plk protein is not stabilized by Hsp90 protein in the cells. For this reason, cells having the gene encoding said mutant Plk protein can not supply a physiologically required amount of Plk protein, which causes abnormalities in the cell such as canceration or the like. According to one embodiment, the present invention provides the aforementioned mutant Plk protein or the aforementioned Plk gene which is involved in formation of malignant tumors.

The present invention further provides:

a method for detecting abnormal cells which comprises the a step of detecting the mutant Plk protein having mutation(s) in the C-terminal domain specified by amino acid residues of from 439 to 603 of the amino acid sequence of the Plk protein wherein the mutation decreases in affinity with Hsp90, or the gene encoding said mutant Plk protein;

use of the mutant Plk protein for detecting abnormal cells, wherein said mutant Plk protein has mutation(s) in the C-terminal domain specified by amino acid residues of from 439 to 603 of the amino acid sequence of the Plk protein and wherein the mutation decreases affinity with Hsp90 protein, or the gene encoding said mutant Plk protein; and use of the mutant Plk protein as a tumor marker, wherein said mutant Plk protein has mutation(s) in the C-terminal domain specified by amino acid residues of from 439 to 603 of the amino acid sequence of the Plk protein, and wherein the mutation decreases affinity with Hsp90 protein, or the gene encoding said mutant Plk protein. An example of the abnormal cells includes malignant tumor cells, and detection of said abnormal cells enables diagnosis of malignant tumors. An embodiment of the use of the aforementioned Plk gene includes detection of the gene capable of interacting with said gene.

Furthermore, the present invention provides the above mutant Plk protein or a homologue thereof which can function in mammalian animals as well as in humans. The invention further provides a method for creating abnormal cells which comprises the step of introducing the gene into cells which encodes the mutant Plk protein having mutation (s) in the C-terminal domain specified by amino acid residues of from 439 to 603 of the amino acid sequence of the Plk protein wherein the mutation decreases affinity with Hsp90; and abnormal cells created by the above method. An example of the abnormal cell includes malignant tumor cells, and creation of these abnormal cells enables establishment of a system for screening antitumor drugs.

From another point of view, the invention provides antibody which specifically recognizes the mutant Plk protein having mutation(s) in the C-terminal domain specified by amino acid residues of from 439 to 603 of the amino acid sequence of the Plk protein wherein the mutation decreases affinity with Hsp90 protein, or specifically recognizes the gene encoding said mutant Plk protein. An example of the antibody preferably include a monoclonal antibody, and the use of this antibody enables detection of malignant tumor cell(s) having the above mutant Plk protein or mutant Plk gene.

By using the mutant Plk protein or the mutant Plk gene provided by the present invention, abnormal cell(s) such as malignant tumor cells can be readily detected, which enables, for example, genetic diagnosis of malignant tumors. Furthermore, the mutant Plk protein is useful for pathologic elucidation, diagnosis, and treatment of malignant tumors or apoptosis-related diseases.

(b) Effect of geldanamycin on the Plk mRNA level; (c) Destabilization of Plk by the treatment with geldanamycin; (d) Disruption of the Plk-Hsp90 complex by the treatment with geldanamycin.

Figure 3:
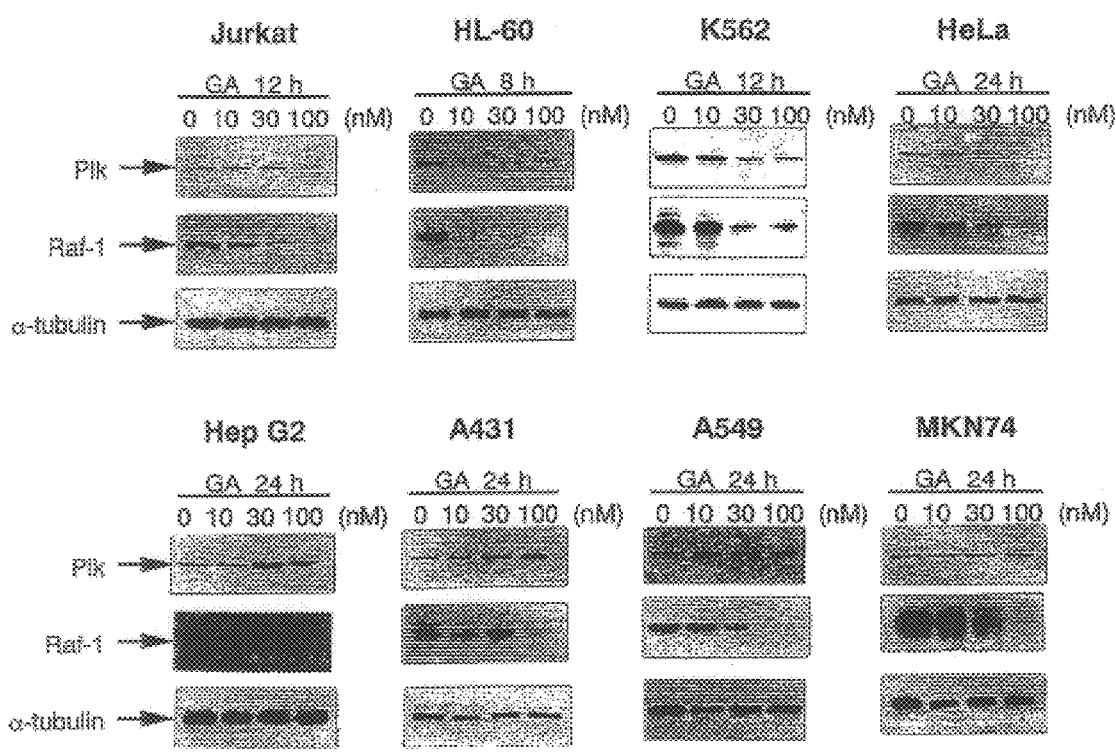

FIG. 3 shows the effect of geldanamycin on degradation of Plk in various human cancer cell lines.

FIG. 4 shows the involvement of the C-terminal domain of Plk in the association with Hsp90: (a) Diagram of GST-fused Plk constructs used in the in vitro binding assay; (b) Results of detection of Hsp90 or α-tubulin associated with GST-fused Plks by Western blotting using an anti-Hsp90 or anti-α-tubulin antibody.

BEST MODE FOR CARRYING OUT THE INVENTION

The mutant Plk protein of the present invention is characterized by having mutation(s) in the C-terminal domain specified by amino acid residues of from 439 to 603 of the amino acid sequence of wild type Plk protein, wherein the mutation decreases affinity with Hsp90 protein. The gene of the invention encodes the above mutant Plk protein of the invention (this gene may be referred to as "mutant Plk gene" hereinafter in the specification). A protein or a gene partly containing the above mutant Plk protein or the mutant Plk gene therein also falls within the scope of the invention. Furthermore, a partial polypeptide containing the C-terminal domain or a partial polynucleotide containing a region encoding the C-terminal domain also falls within the scope of the invention.

The wild type Plk protein is described in Golsteyn, R. M., et al., J. Cell Sci., 107, 1509–1517, 1994; Hamanaka, R., et al., Cell Growth Differ., 5, 249–257, 1994, which has a kinase domain at the N-terminus (53 to 304), a polo-box domain (410 to 438), and C-terminal domain (439 to 603) as shown in FIG. 4a. The mutant Plk protein of the invention is characterized in that the protein has at least one mutation of one or more amino acid residues in the above C-terminal domain, and that the mutation decreases affinity with Hsp90 protein. The term "mutation" as used herein means a mutation where one or more amino acid residues are involved, and the term includes substitution, insertion, and/or deletion.

Hsp90 protein is explained in detail in Buchner, J., TIBS, 24, 136–141, 1999; Protein, Nucleic Acid, Enzyme, 41, 883–887, 1996 as reviews, and a method for observing an interaction between various proteins and the Hsp90 protein is well-known by those skilled in the art. An assay procedure for determining the affinity of the wild type Plk protein or the mutant Plk protein of the invention with Hsp90 protein is described specifically and in detail in examples of the specification. Accordingly, those skilled in the art can readily determine a decrease in affinity of the mutant Plk protein of the invention with Hsp protein, as compared with the affinity of the wild type Plk protein, by referring to the described assay procedure and optionally applying appropriate modifications or variations thereto. The term "a decrease in affinity" or a synonym thereof means a substantial decrease in affinity, including a qualitative or quantitative decrease in interactions as well as a decrease in physicochemical binding strength, and the term should not be interpreted in any limiting way.

The molecular weight of the mutant Plk protein encoded by the mutant Plk gene of the invention is approximately 64 k Da, and the protein is specifically expressed in abnormal cells, especially in malignant tumor cells. This mutant Plk protein has a decreased affinity with Hsp90 protein and poor intracellular stability, thereby the malignant tumor cells having the mutant Plk gene fail to preserve a required amount of the Plk protein in the cell. Thus, by detecting the mutant Plk protein or the mutant Plk gene of the present invention as a marker for abnormal cells, preferably for the malignant tumors, diagnosis of abnormal cells, preferably the malignant tumors are attainable. For example, the malignancy can be determined by measuring expression level of the mutant Plk protein in the cells, and metastasis of malignant tumor cells can be detected by measuring distribution of the mutant Plk protein in vivo. Furthermore, by detecting a gene capable of interacting with the above mutant Plk gene, a gene relevant to the malignant tumors can be identified.

The mutant Plk protein or the mutant Plk gene of the present invention can be readily produced by usual genetic engineering techniques (e.g. Molecular Cloning $2^{nd}$ Ed., Cold Spring Harbor Lab. Press, 1989; A sequel to the Lecture on biochemical experiments, "Gene organon I, II, III", Japan biochemical association eds., 1986), and furthermore, a protein or a gene as a homologue capable of functioning in mammalian animals (e.g. dog, monkey, horse, pig, sheep, cat and the like) as well as in humans can also be produced easily and utilized by those skilled in the art. As one embodiment of a use of the gene of the present invention, for example, abnormal cells accompanying with abnormal cell division can be created by introducing the mutant Plk gene of the invention into the cells. As such abnormal cells, malignant tumor cells can be artificially created, which can be used for screening of anti-tumor drugs. Methods for introducing the mutant Plk gene into the cells are not particularly limited, and usual methods available to those skilled in the art can be appropriately applied. Whether or not the cells after gene introduction produces the mutant Plk protein can be readily detected according to a method specifically described in the examples of the specification.

Specifically, a cDNA library is prepared from a suitable source which expresses the mutant Plk gene of the present invention according to usual methods, and a desired clone can be selected therefrom using an appropriate probe or an antibody specific to the above gene to obtain the mutant Plk gene of the present invention [e.g. Proc. Natl. Acad. Sci., USA., 78, 6613, 1981; Science, 222, 778, 1983]. Examples of a cDNA origin include various cells/tissues which express the gene of the present invention or cultured cells derived therefrom. Isolation of the total RNA therefrom, isolation or purification of mRNA, or obtainment and cloning of cDNA can be performed according to usual methods. Furthermore, cDNA libraries are commercially available, and those cDNA libraries or brain cDNA derived from a newborn mouse can also be used.

A method for screening the mutant Plk gene from a cDNA library is not particularly limited, and usual methods can be applied. Specifically, examples of such methods include a method for selecting a corresponding cDNA clone by immunological screening with the antibody specific to said protein, relative to proteins produced by cDNA; plaque hybridization or colony hybridization with a probe which selectively binds to the desired DNA sequence, or a combination of these methods. As a probe, a DNA which is chemically synthesized based on the base sequence of the mutant Plk gene may be generally used. It is also preferable to use already obtained mutant Plk gene or a fragment thereof. Furthermore, sense and antisense primers which are designed based on the nucleotide sequence information of the mutant Plk gene can also be used as probes for screening.

In obtaining the mutant Plk gene, DNA/RNA amplification by PCR [Science, 230, 1350 (1985)] can be preferably used. When the full-length cDNA is difficult to obtain from a library, application of such methods as RACE method [Rapid amplification of cDNA ends; Experimental medicine, 12(6), 35, 1994], particularly 5'-RACE method [M. A. Frohman, et al., Proc. Natl. Acad. Sci., USA., 8, 8998, 1988] is preferred. Primers used in the application of such PCR methods can be designed appropriately based on the sequence information of the mutant Plk gene elucidated by the present invention, which can be synthesized according to usual methods. Isolation/purification of the amplified DNA/RNA fragments can be performed by usual methods, for example, gel electrophoresis. The nucleotide sequence of the mutant Plk gene or various DNA fragments obtained above can be determined by usual methods such as dideoxy method [Proc. Natl. Acad. Sci., USA., 74, 5463, 1977], Maxam-Gilbert method [Methods in Enzymology, 65, 499, 1980] and the like, or more easily, by using a commercially available sequence kit.

By using the thus mutant Plk gene obtained, for example, by using a partial or the whole nucleotide sequence of the gene, the presence or absence of expression of the mutant Plk gene in individuals or various tissues can be specifically detected. Such detection can be performed by usual methods, for example, RT-PCR-SSCP. Furthermore, by using the mutant Plk gene of the present invention, the expression product of the gene (the mutant Plk protein) or a protein containing the same can be readily produced in large amounts by usual genetic engineering techniques.

The mutant Plk protein of the present invention can be prepared based on the sequence information of the Plk gene provided by the present invention according to usual gene recombinant techniques [Science, 224, 1431, 1984; Biochem, Biophys. Res. Comm., 130, 692, 1985; Proc. Natl. Acad. Sci., USA., 80, 5990, 1983]. More specifically, production of the protein is carried out by creating a recombinant DNA (an expression vector) which allows expression of the gene encoding the desired protein in host cells, transforming the host cells by introducing the DNA into the cells, culturing the resulting transformant, and then collecting the desired protein from the resulting culture.

As the above host cells, either prokaryotes or eukaryotes can be used. As prokaryotic host cells, generally used cell such as *Escherichia coli* or *Bacillus subtilis* can be used. *Escherichia coli*, in particular, *Escherichia coli* K12 strain is preferable. Examples of eukaryotic host cells include craniate cells, yeast cells and the like. Examples of preferably used craniate cells include COS cell (cell from monkey) [Cell, 23, 175, 1981], Chinese Hamster Ovary cells and the dihydrofolate reductase defective strain derived therefrom [Proc. Natl. Acad. Sci., USA., 77, 4216, 1980] and the like, and examples of preferably used yeast cells include *Saccharomyces cerevisiae* or the like. However, cells to be used are not limited to these examples.

When prokaryotic cells are used as host cells, a vector replicable in the host cells may be used. An expression plasmid can be preferably used in which a promoter, an SD sequence (Shine-Dalgarno sequence), and an initiation codon (e.g. ATG) required for starting protein synthesis are provided in the vector upstream of the gene of the present invention to facilitate expression of the gene. Examples of the above vector include generally-used plasmids derived from *E. coli* such as pBR322, pBR325, pUC12, pUC13 and the like. However, applicable vectors are not limited to these examples and various known vectors can also be used. Examples of commercially available vectors usable in expression system using *E. coli* include pGEX-4T (Amersham Pharmacia Biotech), pMAL-C2, pMAl-P2 (New England Biolabs), pET21/lacq (Invitrogen), pBAD/His (Invitrogen) and the like.

As an expression vector of the mutant Plk gene, an ordinary expression vector for a fusion protein is preferably used. An example of the vector includes pGEX (Promega) to express as a fusion protein with glutathion-S-transferase (GST). Methods for introducing a desired recombinant DNA (as an expression vector) into host cells and methods for transformation thereby are not particularly limited, and various generally-used methods can be applied.

The mutant Plk protein of the present invention can be preferably used as an immunogen for creating the specific antibody thereto, and by using this antigen, the desired antiserum (polyclonal antibody) and monoclonal antibody can be obtained according to usual methods. Thus, the present invention provides the antibody which specifically recognizes the mutant Plk protein. An example of the preferable antibody includes the antibody which specifically recognizes a portion of the mutant Plk protein that includes the mutation, and exhibits no activity against the wild type Plk protein. Using this antibody, malignant tumor cells having the above mutant Plk protein can be detected. Furthermore, the above antibody can be used, for example, in purification of the mutant Plk protein, and the measurement or identification thereof by immunological techniques.

For example, by using the antibody to the mutant Plk protein, the wild type Plk and/or the mutant Plk can be measured, which enables detection of malignant tumors. For example, the use of the antibody (a polyclonal or a monoclonal antibody) enables quantification of the mutant Plk protein contained in Plk proteins and detection of the presence/absence of the mutant Plk protein in cells. Plk proteins can be immunoprecipitated from a sample solution containing a biosample such as blood or serum collected from a human, and the resulting proteins can be subjected to reaction with the antibody which recognizes the mutant Plk protein on Western blot or immunoblot using polyacrylamide gel. Furthermore, by using the antibody which recognizes the mutant Plk protein, the mutant Plk protein in a paraffin or frozen tissue specimen can be detected by immunohistochemical techniques.

According to the present invention, in order to detect the presence of the mutant Plk gene which promotes oncogenesis, a biological sample such as blood or serum is prepared, optionally followed by extraction of nucleic acids, and analysis of the presence or absence of the mutant Plk gene. As for a detection method, for example, on the basis of information on a mutant Plk gene previously obtained from a sample deriving from a patient with malignant tumors, e.g. information on the mutation site(s) and mutant sequence of the mutant Plk gene, the mutant DNA fragment can be created, and a probe used for screening and/or amplification of the mutant gene can be designed. More specifically, those having properties as probes for plaque hybridization, colony hybridization, Southern blotting, Northern blotting and the like, and those having properties as proves for obtaining an amplified mutant DNA fragment by polymerase chain reaction (PCR), in which the nucleic acid sequence is amplified with polymerase, can be created. By using primers created for that purpose as a probe for screening and subjecting to reaction with a biological sample (a nucleic acid sample), the presence of a gene having a sequence of the mutant Plk can be verified. The sample of nucleic acids may be prepared by various methods which facilitates the detection of a target sequence, such as degeneration, restrictive digestion, electrophoresis, or dot blotting.

DNA fragments used as primers may be chemically synthesized oligo DNAs, which can be synthesized by an automated DNA synthesizer, for example, DNA synthesizer (PharmaciaLKB Gene Assembler Plus: Pharmacia). The length of synthesized primers (sense primers or antisense primers) is preferably about from 10 to 30 nucleotides. Although a labeled probe is usually used for the above screening, the probe may be unlabeled. Detection can be achieved by specific binding with a directly/indirectly labeled ligand. Suitable labels as well as methods for labeling probes and ligands are known in the art, which includes a radioactive label, biotin, fluorescent group, chemiluminescent group, enzyme, or antibody which can be incorporated by known methods such as nick translation, random priming, or kinase treatment.

An example of a PCR method used for detection includes RT-PCR, and various modifications used in the art can be applied. The use of PCR enables the determination of the presence of the wild type Plk gene and/or a mutant Plk gene, and quantification of DNAs of these genes. Examples of said method include a competitive quantification method such as MSSA (Kinoshita, M., et al., CCA, 228, 83–90, 1994) or PCR-SSCP method (Orita, M., et al., Genomics, 5, 874–879, 1989) which is known as a method for detecting mutations utilizing a change in mobility resulting from a change in higher-order structure of a single-strand DNA.

In the above detection, usable test samples containing the mutant Plk gene (DNA) subjected to measurement are not limited so far that the sample contain said DNA. Examples include biomaterials from a living body such as blood, serum, urine, excised tissue and the like. DNA of the mutant Plk gene can be extracted, purified, and prepared from these test samples according to usual methods.

According to the present invention, for detecting neoplasms, progress to a malignant pre-disorder, or the presence of the mutant Plk gene as a prognostic indication, a biological sample with a disorder can be prepared and then subjected to analysis of the presence or absence of a neoplastic mutant gene of Plk. The use of this method enables, for example, diagnosis of malignant tumors, assessment of therapeutic effect, and prognostic prediction.

Examples of a method for screening a medicament include, for example, a method in which eukayotic host cell lines containing a gene among the mutant Plk genes which encodes a disfunctional mutant Plk protein are used, or a method in which cells containing the mutant Plk gene encoding unstable mutant Plk proteins are used. The host cell lines or the cells are allowed to proliferate in the presence of a test drug for a given period, and then Plk activity is measured after treatment with a drug which acts during mitosis, thereby whether or not the drug is capable of promoting Plk activity is determined.

EXAMPLES

The present invention will be more specifically explained by way of examples. However, the scope of the present invention is limited to these examples.
(A) Methods
(a) Western Blotting The cells were lysed with TENSV buffer (Schulte, T. W., et al., J. Biol. Chem., 270, 24585–24588, 1995; Hutchison, K. A., et al., J. Biol. Chem., 267, 13952–13957, 1992) at 4° C. with sonication. The lysates were subjected to electrophoresis on an SDS polyacrylamide gel. Proteins were transferred to Immobilon PVDF membrane (Millipore) and immunoblotted with anti-Plk antibody (Zymed and Santa Cruz), anti-Hsp90 antibody (AC88; Stressgen), anti-GST antibody (Santa Cruz), anti-α-tubulin antibody (Amersham), or anti-Raf-1 antibody (Santa Cruz). Detection was performed with an enhanced chemiluminescence reagent (Pierce).
(b) Detection of Plk mRNA Level To detect the expression level of Plk mRNA, an RT-PCR assay was performed according to the manufacturer's protocol. The efficiency of the RT reaction and the amount of RNA used in the RT-PCR were verified by detection of the human glyceraldehyde-3-phosphate dehydrogenase (GAPDH) mRNA with RT-PCR (Togashi, K., et al., Oncol. Res., 10, 449–453, 1998). The PCR reaction mixture contained sense and reverse primers and 1 unit of Ampli Taq Gold™ (Perkin Elmer). Amplification was performed for 22 cycles (94° C. for 45s, 60° C. for 45s, and 72° C. for 2 min) in a thermal cycler.
(c) Metabolic Labeling for Plk Cells were cultured in RPMI 1640 medium containing 10% dialyzed FBS and 100 $\mu$Ci ml$^{-1}$ [$^{35}$S]methionine (ICN Biomedicals Ins.) for 2 hours. The cells were subsequently washed with a medium containing nonradioactive methionine, and were treated with geldanamycin for 3 to 12 hours. After drug treatment, the cells were lysed with TENSV buffer at 4° C. for 2 h. The lysates were precleared by removing non-specific binding proteins with protein A-Sepharose (Amersham) and incubated with an anti-Plk antibody at 4° C. for 2 h. The immune complexes were collected by immunoprecipitation and then subjected to electrophoresis. The radiolabelled proteins were visualized by fluorography. The band intensities were quantified using Fujix BAS2000 image analyzer.
(d) Detection of Plk-Hsp90 Complex The cells were lysed with TENSV buffer at 4° C. for 2 h. Aliquots of cell lysates were precleared by removing non-specific binding proteins with protein A-Sepharose or protein G PLUS-Agarose (Santa Cruz) and incubated with anti-Hsp90 antibody or anti-Plk antibldy, respectively. The immune complexes were collected by centrifugation, electrophoresed, transferred to Immobilon membrane and immunoblotted with anti-Hsp90 or anti-Plk antibody.
(e) Plasmid Constructs Human full-lengrh Plk cDNA was isolated from several human cancer cell lines by RT-PCR. The following primers were used to amplify Plk:

5'-CATGAGTGCTGCAGTGACTGCAG-3'    (SEQ ID NO: 1)

and

5'-GACAAGGCTGTAGAACCCACAC-3'    (SEQ ID NO: 2)

The PCR products were cloned into pGEM-T Easy vector (Promega) and nucleotide sequence analysis was carried out by using the dideoxynucleotide chain-termination procedure with an Applied Biosystems automated sequencer. The sequence was confirmed to be identical with a previous report (Golsteyn, R., et al., J. Cell Sci., 107, 1509–1517, 1994). Plk cDNA was inserted into pGEX-2T, and GST-fused Plk was expressed in DH5α with 0.1 mM isopropyl β-D-thiogalacto-pyranoside.
(f) In vitro Binding Assay For the binding assay, 1 $\mu$g of GST-fused proteins was incubated with the lysate of HL-60 cells (1 mg) in TENSV buffer. GST-fused Plk proteins were precipitated with glutathione-agarose (Sigma). Hsp90 or α-tubulin associated with GST-fused Plk proteins was detected by Western blotting using an anti-Hsp90 or anti-α-tubulin antibody.

(B) Results
(a) Mutations within the C-terminus of Plk in Human Cancer Cell Lines It has been suggested that the loss of function or low expression levels of the checkpoint genes may contribute to tumorigenesis in human cancer. Therefore, we first analyzed the expression of Plk protein in human cancer cell lines by Western blotting. High expression level of Plk protein is observed in leukemia (U937, HL-60, Jurkat and K562) and HeLa cells (FIG. 1a), whereas the level of Plk protein is relatively low in other solid cancer cell lines (A431, Hep G2, A549 and MKN74; FIG. 1a). However, the level of Plk mRNAs was similar in U937, Hep G2 and A431 cells (FIG. 1b). Thus, it is suggested that the stability of Plk protein in human cancer cells is regulated by the post-transcriptional mechanism.

To examine whether the low expression levels of Plk protein correlate with the mutations of Plk protein, we next analyzed Plk mutations in human cancer cell lines. We found that Plk harbors mutations in the cancer cell lines, Hep G2, A431, MKN74 and A549, within its C-terminus (Table 1), and no mutation was found in the kinase domain or the polo-box region. On the other hand, we did not find any mutations in the C-terminus of Plk in leukemia cell lines (U937, HL-60, Jurkat and K562) and HeLa cells (Table 1). These results indicate that the mutations in the C-terminus of Plk correlated with the low expression level of Plk protein.

TABLE 1

| Cell line | Origin | Sequence* | Plk protein level** | Sensitivity of Plk to GA*** |
|---|---|---|---|---|
| U937 | promonocytic leukemia | wt | +++ | + |
| HL-60 | promyelocytic leukemia | wt | +++ | + |
| Jurkat | T cell leukemia | wt | +++ | + |
| K562 | erythroleukemia | wt | +++ | + |
| HeLa | cervical carcinoma | wt | +++ | + |
| Hep G2 | hepatoma | N496S, R512W | ± | − |
| A431 | epidermoid carcinoma | S487G, P509S | ± | − |
| A549 | lung adenocarcinoma | D457G | + | − |
| MKN74 | gastric carcinoma | E569K | ++ | − |

*The presence of mutations in human cancer cell lines as determined by sequence analysis. wt; wild-type.
**Plk protein level was detected by Western blotting as shown in FIG. 1a. The Plk protein level was expressed as a relative amount to that in U937 cells as standard (1.0) and classified as times of the mean values. (+++) >0.5; (++) >0.2; (+) >0.05; (±) <0.05;
***Sensitivity of Plk protein to geldanamycin (GA) was assessed by Western blotting as shown in FIG. 3. (+); Plk protein decreased after GA treatment. (−); Plk protein did not decrease after GA treatment.

(b) Regulation of the Stability for Plk Protein by Hsp90.

We hypothesized that a molecular chaperone was probably required to stabilize Plk protein. Our attention was drawn to Hsp 90, a molecular chaperone that is associated with the folding of signal-transducing proteins such as no less than 10 protein kinases (Caplan, A., Trends Cell Biol., 9,262–268, 1999; Buchner, J., Trends Biochem. Sci., 24, 136–141, 1999). The benzoquinone ansamycin, geldanamycin, has been shown to bind specifically and directly to Hsp90, leading to destabilization of v-Src (Whitesell, L., et al., Proc. Natl. Acad. Sci. USA, 91, 8324–8328, 1994), Raf-1 (Schulte, t. W., et al., J. Biol. Chem., 270, 24585–24588, 1995; Schulte, T. W., et al., Mol. cell. Biol., 16, 5839–5845, 1996), and Cdk4 (Dai, K., et al., J. Biol. Chem., 271, 22030–22034, 1996). Whether Hsp90 regulates the stability of Plk protein was investigated.

Treatment of human leukemia U937 cells that have wild-type Plk (Table 1) with 100 nM geldanamycin decreased the level of Plk (FIG. 2a). Although geldanamycin at 100 nM led to the destabilization of Raf-1 in U937 cells at 12 hours without decreasing cell viability, the majority of cells died after 2 days (15.4±3.2%). The time required for geldanamycin treatment to decrease the level of Plk protein was closely related to that for destabilizing Raf-1 (FIG. 2a). RT-PCR analysis of total RNAs from geldanamycin-treated U937 cells revealed the drug did not alter the level of Plk mRNA even at 12 hours (FIG. 2b). Metabolic labeling experiments demonstrated that the half-life of Plk protein in control U937 cells was about 7 hours, while that in geldanamycin-treated cells was about 4 hours; i.e., geldanamycin shortens the half-life of Plk protein (FIG. 2c). Similar results were observed in cells treated with radicicol (Sharma, S., et al., Oncogene, 16, 2639–2645, 1998), another Hsp90 inhibitor. These results demonstrate that geldanamycin-induced reduction of cellular Plk protein is due to the destabilization of the Plk protein and not as a result of decreased gene expression of mRNA. Moreover, geldanamycin-induced destabilization of Plk protein was inhibited by the proteasome inhibitor, MG132, suggesting that proteasome was involved in the pathway of geldanamycin-induced degradation of Plk protein. In the case of Raf-1 protein, geldanamycin-induced destabilization depends on proteasome (Shulte, T. W., Biochem. Biophys. Res. Commun., 239, 655–659, 1997).

To show whether Plk directly binds to Hsp90 in cells, an immunoprecipitation assay was used. Immunoprecipitation of Plk resulted in the coprecipitation of Hsp90 (FIG. 2d, top panel) while immunoprecipitation of Hsp90 coprecipitated Plk (FIG. 2d, middle panel). Coprecipitation of Hsp90 with Plk disappeared after treatment with geldanamycin (FIG. 2d). Although cellular Plk protein was significantly reduced in geldanamycin-treated cells, drug treatment decreased the amount of Plk to one-half by immunoprecipitation (FIG. 2d). The immunoprecipitation technique also provides qualitative data that demonstrates the geldanamycin disrupts the Plk-Hsp90 complex. Similar results have been observed with the Hsp90-Raf-1 complex (Schulte, T. W., J. Biol. Chem., 270, 24585–24588, 1995). Thus it is concluded that Plk directly binds to Hsp90 and this complex is dissociated by geldanamycin. Free Plk protein in the cell is probably targeted for degradation.

(c) Effect of Geldanamycin on the Stability for Plk Protein in Human Cancer Cell Lines To analyze whether the mutations of Plk alter the sensitivity of Plk degradation to geldanamycin, the level of Plk protein in human cancer cell lines treated with geldanamycin was examined. All of these cancer cell lines showed a marked reduction of Raf-1 protein after geldanamycin treatment (FIG. 3). Although the protein level of Plk decreased after the geldanamycin treatment in wild-type Plk-expressing cells (Jurkat, HL-60, K562, and HeLa cells), the level of Plk did not decrease in mutant Plk-expressing cells (Hep G2, A431, A549, and MKN74 cells) (FIG. 3). Therefore, it is demonstrated that Plk protein is not regulated by Hsp90 in mutant Plk-expressing cancer cells.

(d) Involvement of the C-terminus of Plk Protein in Binding to Hsp90

The low expression level of Plk protein in mutant Plk-expressing cells may be due to the instability of Plk protein caused by the instability of Plk-Hsp90 complex. To directly determine whether the mutations of Plk in the C-terminal affected its ability to form the Plk-Hsp90 complex, the interaction of several different GST-fused Plk constructs with the total lysate of HL-60 cells was measured (FIG. 4a). These immunoprecipitation studies demonstrated that, while Hsp90 can bind to full-length Plk as well as the kinase negative Plk mutant, K82R (Golsteyn, R. M., J. Cell Biol., 129, 1617–1628, 1995), the Plk/Hep G2 and Plk/A431 mutants were unable to bind to Hsp90 (FIG. 4b). Therefore, it is suggested that mutations in the C-terminus of Plk disturb the association with Hsp90 and that the protein level of Plk in cells is determined by the interaction between Plk and Hsp90 (FIG. 1a). To establish the region of Plk that is necessary for the interaction with Hsp90, several deletion mutants of Plk were prepared, which were tested using an in vitro binding assay. Hsp90 was found to interact with Plk Δ 185 (which has a half of the kinase domain), but not to the Plk 408 (reduced polo-box and C-terminal domains) nor the Plk 440 (reduced C-terminal domain) (FIG. 4b). These results demonstrate that the C-terminus of Plk protein is necessary for its interaction with Hsp90. Recently, it has been reported that the kinase domain of Plk is required for its binding to tubulins (Feng, Y. et al., Biochem. J. 339, 435–442, 1999). As expected, Plk/Hep G2, Plk/A431, Plk408 and Plk440 had little effect on the association of tubulin with Plk, whereas only a trace amount of α-tubulin was detected in the complex with Plk Δ 185 mutant (FIG. 4b).

Figure 1:
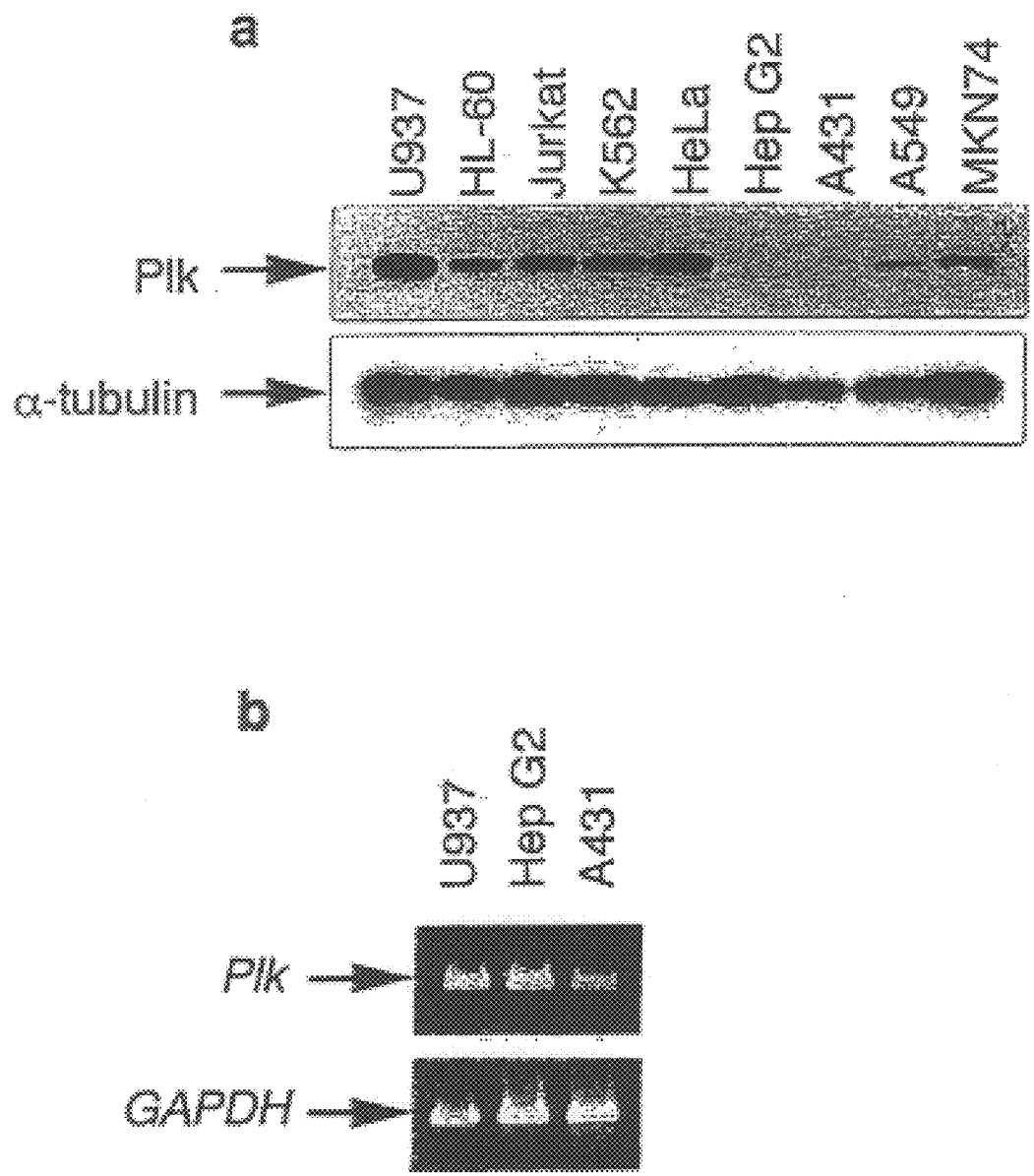
FIG. 1 shows expression of Plk protein and of Plk mRNA in human cancer cell lines: (a) Results of detection of Plk protein levels in various cancer cell lines; (b) Plk mRNA levels in U937, Hep G2 and A431 cells.

FIG. 1 shows expression of Plk protein and of Plk mRNA in human cancer cell lines. a; Detection of protein levels of Plk in various cancer cell lines. Exponentially growing cells were lysed and aliquots of cell lysates were immunoblotted with the indicated antibodies. b; The level of Plk mRNA in U937, Hep G2, and A431 cells. Total RNAs were isolated from the cells, and Plk and GAPDH mRNAs were detected by RT-PCR method.

Figure 2:
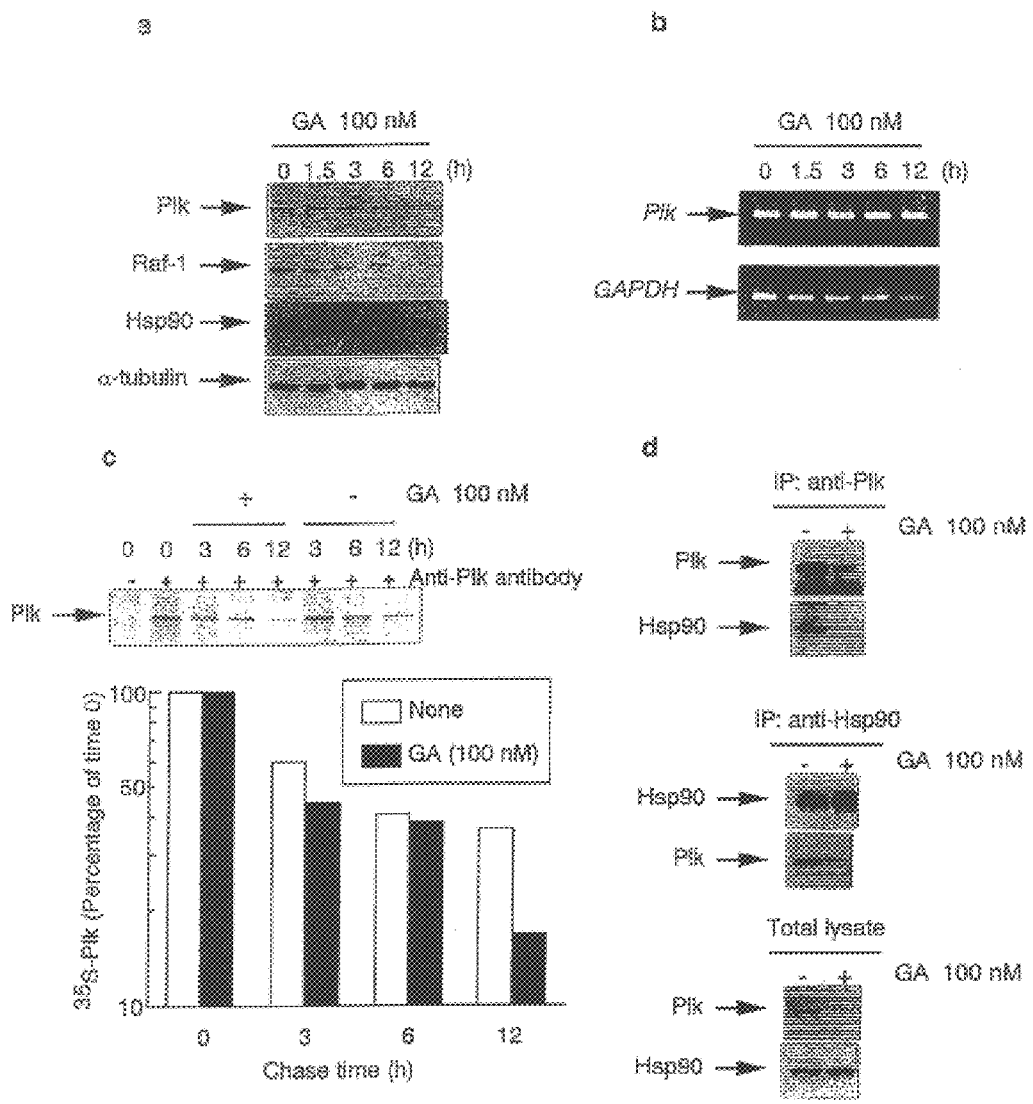
FIG. 2 shows regulation of the stability of Plk protein by Hsp90: (a) Decrease in Plk protein level by geldanamycin.

FIG. 2 shows regulation of the stability of Plk protein by Hsp90. a; Decrease in Plk protein level by geldanamycin. U937 cells were treated with 100 nM geldanamycin for the indicated times. Aliquots of cell lysates were immunoblotted with various antibodies. b; Effect of geldanamycin on Plk mRNA level. U937 cells were treated with 100 nM geldanamycin for the indicated times. Total RNAs were extracted, and Plk and GAPDH mRNAs were detected by RT-PCR. c; Destabilization of Plk by the treatment with geldanamycin. U937 cells were labeled with [$^{35}$S] methionine and treated with or without 100 nM geldanamycin for 3 to 12 hours. The immune complexes were collected by immunoprecipitation using anti-Plk antibody and electrophoresed on an SDS-polyacrylamide gel. The radiolabelled proteins were visualized by fluorography, and band intensities were quantified. d; Disruption of Plk-Hsp90 complex by the treatment with geldanamycin. U937 cells were treated with or without 100 nM geldanamycin for 12 hours. Aliquots of cell lysates were immunoprecipitated with an anti-Plk or anti-Hsp90 antibody. In the same manner, aliquots of non-immunoprecipitated cell lysates were used for Western blotting.

FIG. 3 shows the effect of geldanamycin on Plk degradation in various human cancer cell lines. The cells were treated with various concentrations of geldanamycin for the indicated times. Aliquots of cell lysates were immunoblotted with the indicated antibodies.

FIG. 4 shows involvement of C-terminal domain of Plk in its binding to Hsp90. a; Diagram of GST-fused Plk constructs used in the in vitro binding assay. The circle stands for the GST protein, the dotted bar for the kinase domain (residues 53–305) and the black box for the polo-box (residues 410–439). b; GST-fused Plks, expressed in *Escherichia coli*, were collected with glutathione-agarose, and incubated with the lysate of HL-60 cells. After incubation, GST-fused Plks were precipitated with glutathione-agarose. Hsp90 or α-tubulin associated with GST-fused Plks was detected by Western blotting using an anti-Hsp90 or anti-α-tubulin antibody.

The present disclosure relates to subject matter contained in priority Japanese Patent Application No. 2000-163122, filed on May 31, 2000, the contents of which is herein expressly incorporated by reference in its entirety.

What is claimed is:

1. An isolated mutant Plk protein having at least one of S487G, P509S, N496S and R512W mutation in C-terminal domain of wild-type Plk protein, wherein said mutation decreases affinity with Hsp90 protein.

2. An isolated nucleotide sequence encoding the Plk protein according to claim 1.

3. A method of producing an abnormal cell comprising introducing the mutant Plk nucleotide sequence according to claim 2 into a cell.

4. The isolated Plk protein according to claim 1, wherein the mutation in the amino acid sequence comprises S487G and P509S.

5. An isolated nucleotide sequence encoding the Plk protein according to claim 4.

6. The isolated Plk protein according to claim 1, wherein the mutation in the amino acid sequence comprises N496S and R512W.

7. An isolated nucleotide sequence encoding the Plk protein according to claim 6.

* * * * *